United States Patent

Okajima

Patent Number: 5,538,513
Date of Patent: Jul. 23, 1996

[54] CATHETER TUBE HAVING A FILAMENTOUS REINFORCING LAYER

[75] Inventor: Naofumi Okajima, Shizuoka-ken, Japan

[73] Assignee: Terumo Kabushiki Kaisha, Tokyo, Japan

[21] Appl. No.: 139,729

[22] Filed: Oct. 22, 1993

[30] Foreign Application Priority Data

Oct. 23, 1992 [JP] Japan ................... 4-307897

[51] Int. Cl.⁶ ................................................ A61M 25/00
[52] U.S. Cl. ........................ 604/282; 604/280; 138/124
[58] Field of Search ............................ 604/264, 280, 604/282; 128/656–658; 138/123, 124, 125, 126, 127, 137, 138

[56] References Cited

U.S. PATENT DOCUMENTS

| 4,516,972 | 5/1985 | Samson | 604/282 |
|---|---|---|---|
| 4,636,346 | 1/1987 | Gold et al. | 264/139 |
| 4,898,591 | 2/1990 | Jang et al. | 604/282 |
| 5,037,404 | 8/1991 | Gold et al. | 604/282 |
| 5,041,100 | 8/1991 | Rowland et al. | |
| 5,057,092 | 10/1991 | Webster, Jr. | |
| 5,312,356 | 5/1994 | Engelson et al. | 604/164 |

FOREIGN PATENT DOCUMENTS

| 0249338 | 12/1987 | European Pat. Off. |
|---|---|---|
| 0358117 | 3/1990 | European Pat. Off. |
| 0369383 | 5/1990 | European Pat. Off. |
| 59-80257 | 5/1984 | Japan |
| 59-156353 | 9/1984 | Japan |
| 62-17082 | 4/1987 | Japan |
| WO90/14123 | 11/1990 | WIPO |

Primary Examiner—Corrine M. McDermott
Attorney, Agent, or Firm—Burns, Doane, Swecker & Mathis

[57] ABSTRACT

A catheter tube is composed of a main portion and a tip portion. The main portion of the catheter tube is of such a structure that an inner tube and an outer tube are joined via a reinforcing material layer, but the tip portion is of such a structure that only the inner tube and the outer tube are joined without intervening the reinforcing material layer between the two tubes. The reinforcing material layer is formed by arranging a filamentous element (e.g., stainless steel wire) around the inner tube in a lattice manner. The inclination angles $\theta_1$, $\theta_2$ and $\theta_3$ of the filamentous element with respect to the axis of the catheter tube at the first, second and third regions, respectively are determined so as to establish the relationship as $\theta_1 < \theta_2 < \theta_3$. Therefore, the rigidity of the catheter can be increased in accordance with the decrease of the inclination angle of the filamentous element. According to the catheter tube, excellent pushing, torque transmission, follow-up to a guide wire, and kink-resistant characteristics can be attained, simultaneously and respectively.

10 Claims, 3 Drawing Sheets

CATHETER TUBE HAVING A FILAMENTOUS REINFORCING LAYER

BACKGROUND OF THE INVENTION

1. Field of the Invention

The present invention relates to a catheter tube used for a blood vessel catheter, for instance and a method of manufacturing the catheter tube.

2. Description of the Prior Art

Generally, in performing selective angiography or vasodilation, various catheters such as an angiography catheter, a guiding catheter or a balloon catheter or the like are used. In these catheters, it is usually required to have such an excellent manipulatability that can be selectively inserted into a blood vessel system of complicated pattern quickly and securely.

In more detail, the above-mentioned manipulatability of the catheter includes pushing characteristics, torque transmission characteristics, follow-up characteristics and kink-resistant characteristics. The pushing characteristics means that when the catheter is pushed into a blood vessel by an operator, a pushing force of the operator can be securely transmitted from the base end side to the tip side of the catheter. The torque transmission characteristics mean that a rotative force applied to the base end side of the catheter can be securely transmitted to the tip side thereof. The follow-up characteristics mean that when the catheter is inserted into a curved blood vessel, the catheter can travel smoothly along a guide wire going ahead without injuring the inner wall of the blood vessel (hereinafter, referred to as "follow-up to the guide wire" or simply "follow-up"). The kink-resistant characteristics mean that when the catheter is extracted after having reached at a destination, the catheter will not be bent at a curved or bent position of the blood vessel.

In order to improve the pushing and transmission characteristics, it is so far known that the catheter tube excepting the tip portion thereof is preferably formed of a relatively hard material. Further, in order to improve the follow-up characteristics, it is so far known that the tip portion thereof is preferably formed of a relatively soft material.

On the basis of this knowledge, Japanese Laid-open Patent Publication No. 59-156353 discloses a catheter tube in which a tubular base portion formed of nylon is fused integrally into a tip portion formed of polyether-polyamide copolymer so as to provide an appropriate flexible tip portion of the catheter tube. In this catheter tube, however, since two different materials must be fused for connection, there is a problem in that the connected portion is easily broken off. Further, there is another problem in that a stepped portion is likely to be formed on the outer surface of the catheter tube, which results in that the inner wall of the blood vessel is likely to be injured when the catheter tube is being inserted thereinto. Furthermore, since the rigidity of the catheter tube changes abruptly at the connected portion, the connected portion is likely to be bent, so that the kink-resistant characteristics are deteriorated. In addition, there is a further problem in that a special manufacturing installation is required for fusing the polymers and a complicated manufacturing process is inevitably required.

Further, Japanese Utility Model Publication No. 62-17082 discloses a catheter tube which comprises an outer tube and an inner tube inserted into the outer tube excepting the tip portion of the outer tube, in which the outer tube is formed of a silicone rubber and the inner tube is formed of a hard resin selected from the group consisting of polyethylene, polypropylene, fluororesin and hard vinyl chloride resin. In the catheter tube as disclosed above, however, since a stepped portion which corresponds to the thickness of the inner tube is unavoidably formed within the inner hollow portion of the tube at the boundary part between the double-tubes portion (the main body portion 4) and the single-tube portion (the tip portion 3), the tube is likely to be broken off at this stepped portion, thus deteriorating the kink-resistant characteristics.

Moreover, U.S. Pat. No. 4,636,346 discloses a guiding catheter having a catheter tube which comprises a main portion having three-layers structure and a tip end portion having two-layers structure and extending toward the tip of the catheter from the main portion. The main portion is composed of an inner tube, an intermediate layer and an outer tube. The tip end portion is composed of an inner tube and an outer tube, but no intermediate layer is provided. However, the main portion of the catheter tube, having the three-layered structure, has bending rigidity that is constant in the longitudinal section thereof and the bending rigidity changes abruptly at the boundary part between the main portion and the tip portion having the two-layered structure because of the presence or absence of the intermediate layer. As a result, the tube is likely to be broken off at this boundary part, thus deteriorating the kink-resistant characteristics.

SUMMARY OF THE INVENTION

The object of the present invention is to provide a catheter tube excellent in manipulatability such as the pushing, torque transmission, follow-up, kink-resistant characteristics, etc.

The catheter tube according to the present invention comprises a flexible inner tube, an flexible outer tube provided around the inner tube and a reinforcing material layer disposed between the inner and outer tubes. The reinforcing material layer is formed by arranging at least one filamentous element in a lattice manner. Due to the presence of the filamentous element, a sufficient bending rigidity is obtained in a main part of the catheter tube which has three-tube structure, thus improving the pushing and torque transmission characteristics.

The reinforcing material layer is constituted in such a way that inclination angles of the filamentous element with respect to the axis of the catheter tube change continuously or in a stepwise manner along the axial direction so as to form one section thereof in which the inclination angle is relatively large and another section thereof in which the inclination angle is relatively small. As a result, the bending rigidity of the catheter tube at which the one section of the reinforcing material layer is located is smaller in comparison with that of the catheter tube at which the another section of the reinforcing material layer is located.

When the inclination angle of the filamentous element is increased continuously toward the tip side of the catheter tube, the bending rigidity of the catheter tube also decreases continuously. Further, even when the respective inclination angle of the filamentous element is increased stepwise toward the tip side of the catheter tube, it is also possible to decrease the bending rigidity of the catheter tube substantially continuously, by increasing the number of stages of change in inclination angle or by making the change rate of the inclination angles relatively small.

As described above, since the bending rigidity of the catheter can be reduced continuously toward the tip side of the catheter tube, it is possible to realize an excellent follow-up and kink-resistant characteristics.

The reinforcing material layer may be formed of at least one filamentous element which is arranged in a lattice manner in such a way that the respective intervals of the lattice points of the filamentous element along with the axial direction of the catheter tube are changed continuously or stepwise along the axial direction of the catheter tube so as to form one section thereof in which the respective interval between the lattice points of the filamentous element is relatively small and another section thereof in which the respective interval between the lattice points of the filamentous element is relatively large. As a result, the bending rigidity of the catheter tube at which the one section of the reinforcing material layer is located is smaller than that of catheter tube at which the another section of the reinforcing material layer is located.

According to the catheter tube of the present invention as stated in the above, since a sufficient rigidity of the catheter tube can be obtained by the reinforcing material layer, it is possible to obtain excellent pushing and torque transmission characteristics. In addition, by changing the inclination angles or the lattice point intervals of the filamentous element which constitutes the reinforcing material layer along the axial direction of the catheter body, the rigidity of the catheter can be changed well balanced at the respective portions of the catheter, in particular at the tip portion of the catheter. As a result, excellent follow-up to the guide wire characteristics as well as excellent kink-resistant characteristics can be obtained, in addition to the higher safety.

The reinforcing material layer is preferably disposed only at the main portion of the catheter. Further, the outer diameter of the outer tube or the inner or outer diameter of the inner tube may be changed near the tip portion of the reinforcing material layer. Furthermore, the inner and outer tubes can be formed of the same material, or at least the outer tube is formed of a soft material.

Further, when the catheter tube according to the present invention is manufactured, the inclination angles or the lattice point intervals of the filamentous element can be changed by appropriately adjusting the relative movement speed or the relative rotational speed between the inner tube and the filamentous element supply device, and in addition there is no restriction in materials for forming the inner and outer tubes from the physical standpoints. Therefore, it is possible to adjust the rigidity of the catheter at the respective portions freely and securely, thus allowing the catheter tube to be manufactured through an easy process and at a low cost.

Other objects, features and advantages of the present invention will become apparent when the following detailed description of the preferred embodiment is taken in conjunction with the attached drawings.

DETAILED DESCRIPTION OF THE PREFERRED EMBODIMENT

The catheter tube of the present invention will be described in detail hereinbelow on the basis of preferred embodiment with reference to the attached drawings.

Figure 1:
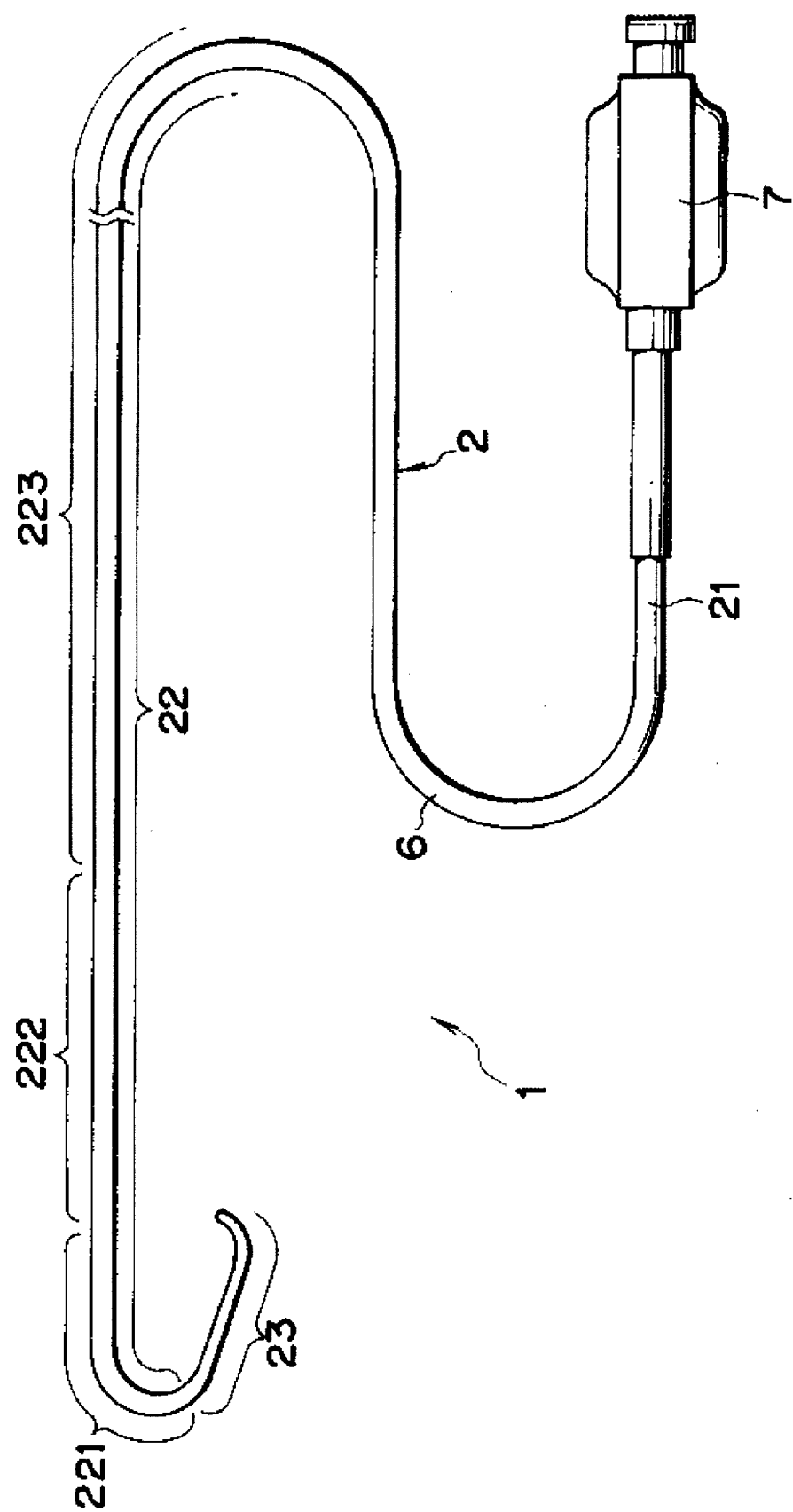
FIG. 1 is a plan view showing an exemplary structure of a catheter assembly including the catheter tube according to the present invention.
Figure 2:
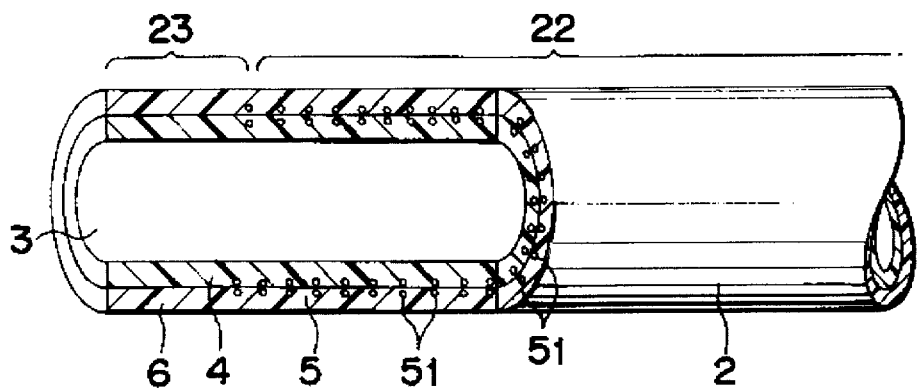
FIG. 2 is an enlarged cross-sectional, partially broken view showing the formation of the reinforcing material layer of the catheter tube shown in FIG. 1.

FIG. 1 is a plane view showing the whole construction of a catheter assembly 1 including the catheter tube according to the present invention, which is constructed as a blood vessel catheter. FIG. 2 shows an enlarged cross-sectional view taken along a line near the tip portion of the catheter tube shown in FIG. 1. Further, in FIG. 2, the catheter tube is shown as a model view by enlarging only the radial direction of the tube, to facilitate understanding of the tube structure.

The catheter assembly 1 shown in FIG. 1 is composed of a catheter tube 2, and a hub 7 attached to a base end 21 of the catheter tube 2. The catheter tube 2 is formed with a lumen 3 extending from the base end 21 to the tip 23 thereof. The lumen 3 serves as a flow path through which a medical liquid or the like is passed. Further, when the catheter tube 1 is inserted into a blood vessel, a guide wire is inserted into the lumen 3.

The hub 7 functions as an inlet portion through which a medical liquid is injected into the lumen 3 and an insertion opening through which the guide wire is inserted. In addition, the hub 7 serves as a grip when the catheter tube 1 is operated.

FIG. 2 shows a state in which a part of the catheter tube 2 is cut off near the tip thereof. As depicted in FIG. 2, the essential portion 22 of the catheter tube 2 is composed of an inner tube 4 and an outer tube 6 both joined together via an intermediate reinforcing material layer 5. Further, the tip portion 23 extending from the essential portion 22 of the catheter tube 2 is composed of the inner tube 4 and the outer tube 6 joined together without intervening the intermediate reinforcing material layer 5 between the two tubes 4 and 6. These inner and outer tubes 4 and 6 are both formed of a flexible (soft) material.

As the material for forming the inner and outer tubes 4 and 6, the following materials can be selectively used, for instance: various flexible resins such as polyolefin such as polypropylene, polyethylene, ethylene-vinyl acetate copolymer or the like; polyamide; polyester such as polyethylene terephthalate, polybutylene terephthalate or the like; polyurethane; polyvinyl chloride; polystyrene resin; fluorine-based resin such as ethylene-tetrafluoro ethylene copolymer; and polyimide etc.; various elastomers such as polyamide elastomer, polyester elastomer, polyurethane elastomer, polystyrene elastomer, fluorine elastomer, silicone rubber, latex rubber or the like; or combinations of two or more of these materials.

Here, the polyamide elastomer is typically block copolymer composed of hard segment and soft segment. As the hard segment, aliphatic or aromatic polyamide such as nylon 6, nylon 64, nylon 66, nylon 610, nylon 612, nylon 46, nylon 9, nylon 11, nylon 12, N-alkoxy methyl denaturation nylon, hexamethylenediamine-isophthalic acid condensation copolymer, or metaxyloyldiamine-adipic acid condensation copolymer or the like can be selectively used. As the soft segment, copolymer such as polyester or polyether or the like can be selectively used. Further, the polyamide elastomer includes polymer alloy of the polyamide and soft resin (polymer blend, graft polymerization, random polymerization, etc.), the polyamide softened by plasticizer, or mixtures of these.

Further, the polyester elastomer is typically block copolymer of saturated polyester (such as polyethylene terephthalate, polybutylene terephthalate) and polyether or polyester. In addition, the polyester elastomer also includes polymer alloy of these materials, saturated polyester softened by plasticizer, or mixtures of these materials or the like.

Further, the same or different materials can be used for the inner tube 4 and the outer tube 6.

As described later in more detail, in the present invention, the balance in rigidity of the respective portions of the catheter 2 is determined by adjusting the inclination angle (or the intervals between lattice points) of a filamentous element 51 of a reinforcing material layer 5 at respective regions 221, 222 and 223 of the catheter 2. Accordingly, the material of the inner tube 4 and the outer tube 6 is not subjected to the restriction of the physical properties (the rigidity and hardness, in particular), so that there is such an advantage that the material thereof can be selected from various materials. In other words, it is unnecessary to adjust the balance in rigidity of the respective portions of the catheter on the basis of a difference in rigidity between the materials used for the inner tube 4 and the outer tube 6, respectively. Further, since the same material can be used for both the inner tube 4 and the outer tube 6, it is possible to facilitate the manufacturing process and thereby to reduce the cost thereof.

Further, when the inner tube 4 and the outer tube 6 are both formed of the same material, it is preferable to use a relatively soft material. This is because the adjustment effect based upon change in inclination angle (or intervals between the lattice points) of the filamentous element 51 becomes more prominent for the rigidity of the catheter tube.

Further, in the case where the material of the inner tube 4 is different from that of the outer tube 6, it is preferable to form the outer tube 6 of a material softer than that of the inner tube 4, in view of the facts that the outer tube 6 is in contact with a living body when used and that the geometrical moment of inertia of the outer tube 6 in its cross section (which affects rigidity of the catheter) is usually larger than that of the inner tube 4.

When the inner tube 4 and the outer tube 6 are formed of the same material or different materials as described above, it is preferable that the Shore D hardness of the material used for the outer tube 6 lies from 40 to 80.

Further, it is also preferable to mix the material for forming the inner tube 4 or the outer tube 6 with an X-ray contrast medium such as metal powder of platinum, gold, tungsten or alloy of these; or barium sulfate, bismuth sulfate or coupling compound of these, in order that the position of the catheter 2 can be recognized visually under the examination of fluoroscopy when the catheter is used.

Further, in the catheter shown in FIG. 2, the inner and outer diameters of the inner and outer tubes 4 and 6 are illustrated to be constant. Without being limited thereto, however, these diameters can be changed in the longitudinal direction of the catheter 2.

For instance, it is possible to decrease the outer diameters of the inner tube 4 or the outer tube 6 gradually, or to increase the inner diameter of the inner tube 6 gradually, toward the tip side of the catheter (hereinafter, referred to as toward the tip side), before and after the position at which the inclination angle (or the intervals between the lattice points) of the filamentous element 51 of the reinforcing material layer 5 (described later in more detail) changes or near the boundary region between the tip portion 23 and the first region 221. In these cases, since the thickness of the inner tube 4 or the outer tube 6 decreases gradually toward the tip side, the rigidity of the catheter tube 2 can also be decreased continuously.

Figure 3:
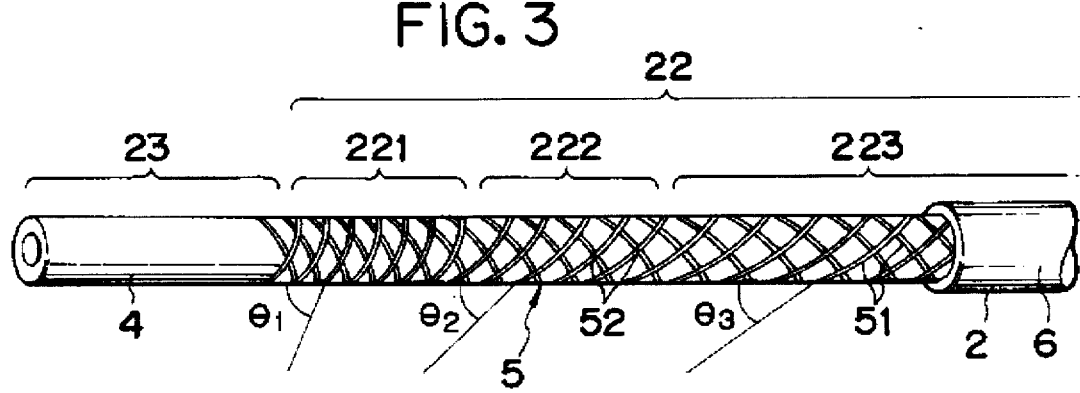
FIG. 3 is a perspective view showing the formation of the reinforcing material layer of the catheter tube shown in FIG. 1.
Figure 4:
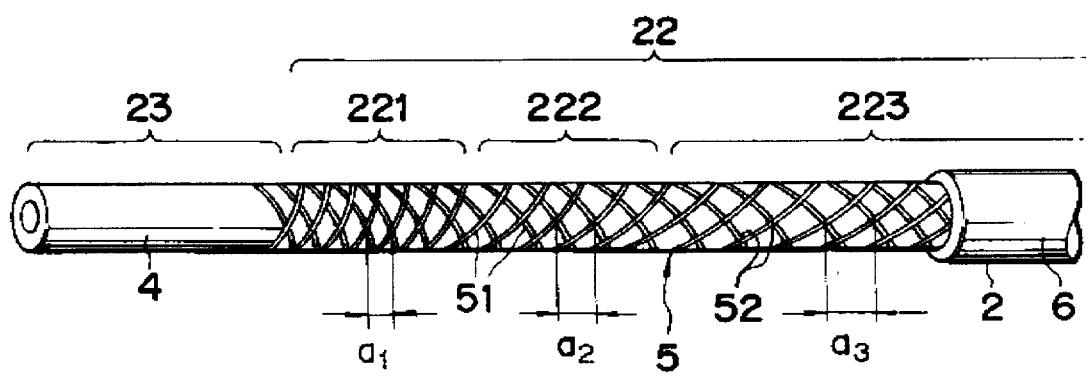
FIG. 4 is a perspective view showing the formation of the reinforcing material layer of the catheter tube shown in FIG. 1.

As shown in FIGS. 2, 3 and 4, the reinforcing material layer 5 is formed from the filamentous element 51 arranged in a lattice manner. For instance, the filamentous element 51 is wound around the outer circumferential surface of the inner tube 4 in helical manner in two different winding directions in such a way that lattice points 52 can be formed at the intersections of the filamentous element 51 helically wound in two different directions.

The main portion 22 of the catheter tube 2 formed with the reinforcing material layer 5 is divided into the first region 221, the second region 222 and the third region 223, respectively beginning from the tip side (from the left side in FIG. 3). Further, the inclination angle of the filamentous element 51 with respect to the axis of the catheter tube is stepwise different from each other at the respective regions 221, 222 and 223. That is, among the inclination angles at the respective regions, there is such a relationship as represented by the following equation:

$$\theta_1 > \theta_2 > \theta_3$$

where $\theta_1$ denotes the inclination angle of the filamentous element 15 with respect to the axis of the catheter tube 2 at the first region 221; $\theta_2$ denotes the inclination angle of the filamentous element 51 at the second region 222; and $\theta_3$ denotes the inclination angle of the filamentous element 51 at the third region 223, respectively.

In the reinforcing material layer 5, since the inclination direction of the filamentous element 51 approaches the axial direction of the catheter tube 2 at the region where inclination angle of the filamentous element 51 is relatively small, the reinforcing effect is increased, so that the rigidity (bending rigidity and twisting rigidity, in particular) of the catheter 2 can be increased. Consequently, when the inclination angles of the filamentous element 51 are changed as described above, it is possible to decrease the rigidity of the catheter tube in the order of the third region 223, the second region 222 and the first region 221. Further, since there is no reinforcing material layer 5 at the tip portion 23, the rigidity at the tip portion 23 becomes lower than that at the first region 221. This means that the softness of the catheter 2 increases in order toward the tip side.

Further, the fact that the inclination angle of the filamentous element 51 increases continuously or stepwise toward the tip side of the catheter tube 2 means the fact that the respective intervals between the lattice points 52 of the filamentous element 51 in the axial direction of the catheter (referred to as lattice point intervals, hereinafter) decreases continuously or in a stepwise manner toward the tip side of the catheter 2. Therefore, among the lattice point intervals at the respective regions, there is such a relationship as represented by the following equation:

$$a_1 < a_2 < a_3$$

where $a_1$ denotes the lattice point intervals of the filamentous element 5 at the first region 221; $a_2$ denotes the lattice point intervals of the filamentous element 5 at the second region 222; and a3 denotes the lattice point intervals of the filamentous element 5 at the third region 223, respectively.

The lengths of the first region 221, the second region 222 and the third region 223, and the inclination angles θ1, θ2 and θ3, and the lattice point intervals a1, a2 and a3 are all not limited, respectively. In the case where the catheter tube of the present invention would be applied to a blood vessel catheter, in particular to an angiography catheter as shown in FIG. 1, the respective values are preferably set in the following ranges:

The lengths of the first region 221 and the second region 22 in the axial direction are from 50 to 300 mm, respectively, but the length of the third region 223 (from the base end portion to the second region 222 in the whole length of the catheter tube) is different according to the kinds of the catheter and therefore not limited thereto.

The inclination angles θ1, θ2 and θ3 are about from 40° to 50°, from 40° to 45°, and from 35° to 40°, respectively.

The lattice point intervals a1, a2 and a3 are from 0.2 to 0.4 mm, from 0.5 to 0.7 mm, and from 0.8 to 1.0 mm, respectively.

When the above-mentioned ranges are adopted, the catheter tube 2 can be well balanced in rigidity at the respective portions, so that it is possible to realize the effects of the present invention described hereinbelow more effectively.

Further, in the embodiment shown in the drawings, the reinforcing material layer 5 is provided for the catheter 2 except the tip portion 23. Therefore, due to such an arrangement, there is such an effect that the tip portion 23 is softer than the inner tube 4 and the outer tube 6 so as to be bendable more easily. Without being limited thereto, however, there is no problem even if the reinforcing material layer 5 is provided for the tip portion 23 of the catheter tube 2.

Figure 5:
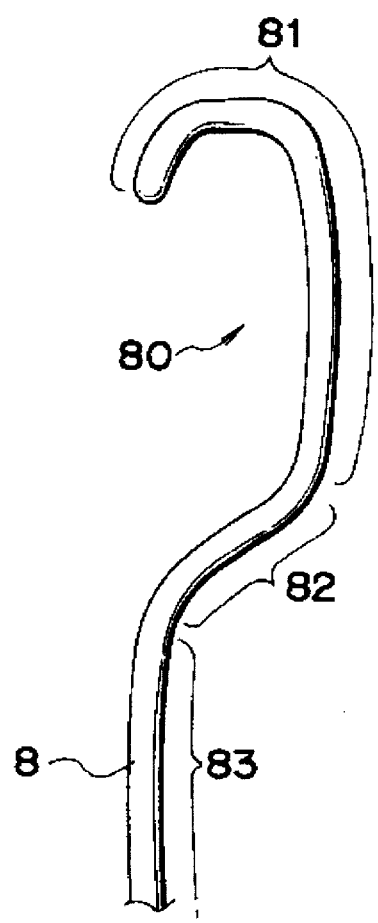
FIG. 5 is a plan view showing another exemplary structure of the catheter tube according to the present invention.

In this connection, it should be noted that in the catheter according to the present invention, the object and the position for and at which the rigidity (or softness) of the catheter tube is adjusted by changing the inclination angle of the filamentous element 51 and the lattice point intervals are not limited to only the above-mentioned descriptions. For instance, in the case of a catheter tube 8 formed with a curved portion 80 at which the tip portion is bent into a hook shape, as shown in FIG. 5, the bent portion 8 is divided into a first region 81, a second region 82 and a third region 83, respectively beginning from the tip portion thereof. In this example, the rigidity of the second region 82 (corresponding to a neck portion at which a stress is likely to be concentrated) is determined to be larger than those of the other first and third regions 81 and 83, so that the bent shape of the whole curved portion 80 can be maintained stably.

Any material can be used for the filamentous element 51 of the reinforcing material layer 5, as far as the rigidity is large enough to provide a sufficient reinforcing effect to the catheter. For example, the following materials can be selectively used: various metallic materials such as stainless steel, copper, tungsten, nickel, titanium, piano wire, superelastic alloy such as Ni—Ti alloy, Ni—Ti—Co alloy, Ni—Al alloy, Cu—Zn alloy, Cu—Zn—X alloy (e.g., X=Be, Si, Sn, Al, Ga), or amorphous alloy or the like; various polymers such as polyester such as PET (polyethylene terephthalate), PBT (polybutylene terephthalate), polyolefin such as polyethylene and polypropylene and so forth, hard polyvinyl chloride, polyamide, polymide, polystyrene, thermoplastic polyurethane, polycarbonate, ABS resin, acrylic resin, PMMA (polymethyl methacrylate), PA (polyacetal), polyacrylate, POM (polyoxymethylene), high tension polyvinyl alcohol, fluorine resin, PVdF (polyvinydelin fluoride), polytetra fluoroethylene, EVOH (ethylene-vinyl acetate saponification), polysulfone, polyethersulfone, polyether ketone, polyphenylene oxide or polyphenyline sulfide or the like; or polymer alloy containing one or more of these polymers; carbon fiber; glass fiber; or a combination of two or more of above mentioned materials. In these materials, stainless steel and PET are particularly preferable from the standpoints of machinability or workability, economics and non-poisonous characteristics.

Further, the filamentous element 51 is formed from a single fiber or an aggregate of fibers (e.g., a stand of fibers) of the above-mentioned material.

Further, the thickness of the filamentous element 51 is determined to such an extent that a sufficient reinforcing effect can be obtained with reference to each of the adopted materials. In the case where the metallic material is adopted, it is preferable to determine the diameter thereof to be from 30 to 50 μm. Further, the filamentous element 51 can be formed by using a single wire or by bundling a plurality of wires.

In the above embodiment, the filamentous element 51 can be formed from a single fiber or bundled many fibers. Further, the reinforcing material layer can be formed from a single continuous filamentous member or from more that two filamentous members.

According to the catheter assembly 2 having the catheter tube 2 as described above, the following advantages can be obtained: The bending elastic modulus of the catheter tube 2 can be well balanced at the respective portions thereof. In particular, a sufficient rigidity can be obtained at the third region 223, so that excellent pushing characteristics and torque transmission characteristics can be realized. Further, excellent follow-up to the guide wire characteristics can be obtained at the first and second regions 221 and 222, so that stimulation applied against the inner wall of the blood vessel can be extremely reduced, and in addition, excellent kink-resistant characteristics can also be obtained.

Further, in the embodiment shown in FIGS. 3 and 4, the inclination angles or the lattice point intervals of the filamentous element 51 are changed into three different stages at the first, second and third regions 221, 222 and 223 of the catheter tube 2, respectively. Without being limited, however, the inclination angles or the lattice point intervals thereof can be changed into two stages or four or more stages. Further, it is also possible to change the inclination angles or the lattice point intervals continuously or steplessly.

In the catheter tube according to the present invention, it is preferable that the outer surface of the catheter tube 2 is covered with a hydrophilic (or water-soluble) high-molecular substance (not shown). This is because when the outer surface of the catheter tube 2 is in contact with blood or physiological saline solution, the frictional coefficient is reduced due to such a substance and thereby the lubrication can be improved, so that the movability or the slidability of the catheter tube 2 can be further improved. As a result, the pushing, follow-up, kink-resistant and safety characteristics can be further improved.

As the hydrophilic high-molecular substance, the following substances can be selectively used: natural or synthetic high-molecular substance, or the derivative thereof. In particular, the following substance is preferable because a low frictional coefficient can be obtained stably: cellulose based high-molecular substance (e.g., hydroxyproyl cellulose), polyethylene oxide based high-molecular substance (e.g., polyethylene glycol), anhydrous maleic acid based high-molecular substance (e.g., anhydrous maleic acid copolymer such as methyvinylether-anhydrous maleic acid copolymer), acrylic amide based high-molecular substance (e.g., polyacrylamide), water-soluble nylon (e.g., AQ-nylon P-70, made by TORAY Industries, Inc., Japan).

Further, the derivative for the above-mentioned high-molecular substances is not limited to water-soluble substances. Non water-soluble substances can be used, as far as the substance has the above-mentioned water-soluble high-molecular substance as the basic composition; the molecular chains thereof are free; and the substance has water absorption characteristics.

In order to form a coating layer of the above-mentioned hydrous high-molecular substance on the outer surface of the catheter tube 2, it is preferable to covalent-bond the above-mentioned substance with a reactive functional radical existing on the surface of the outer tube 6 or introduced into the outer tube 6. By the above-mentioned covalent bonding, it is possible to obtain a stable lubricating surface on the circumferential surface of the outer tube 6.

As the reactive functional radical applied to the surface of or introduced into the outer tube 6, any radicals can be used, as far as the radical is reactive with the above-mentioned high-molecular substance and fixed thereto by bonding or bridging. The preferable radicals or groups are as follows: diazonium radical, azido radical, isocyanate radical, acid chlorido radical, acid anhydride radical, imino carbonate radical, amino radical, carboxyl radical, epoxy radical, hydroxyl radical, aldehyde radical, etc. In particular, isocyanate radical, amino radical, aldehyde radical, and epoxy radical are preferable.

A preferred example of the method of manufacturing the catheter tube according to the present invention will be described hereinbelow.

First, the inner tube 4 is formed in accordance with the conventional method. Thereafter, the filamentous element 51 is wound around the outer circumferential surface of the inner tube 4 in spiral fashion. An apparatus so called as a braider (not shown) is for example used in order to perform the winding. A filamentous element 51 is fed thereto from a supply device of the apparatus, while the inner tube 4 is shifted or moved in the axial direction thereof and further rotated about the axis thereof both relative to the filamentous element supply device. By doing so, the filamentous element 51 can be wound continuously around the outer circumferential surface of the inner tube 4.

In this process, the winding start position of the filamentous element 51 is determined for example at the boundary part between the tip portion 23 and the first region 221 and the inner tube 4 is rotated at a constant speed. Under the condition, if the movement speed of the inner tube 4 in the first (leftward) axial direction thereof is increased gradually in the order of positions of the first region 221, the second region 222 and the third region 223, it is possible to obtain the inclination angles $\theta 1$, $\theta 2$ and $\theta 3$ of the filamentous element 51 as disclosed before.

After the filamentous element 51 has been wound onto the base end portion 21 by moving the inner tube 4 in the first axial direction of the catheter tube 2, the inner tube 4 is then moved in a second (rightward) axial direction, while the inner tube 4 is kept rotated and the filamentous element 51 is kept fed, and then being stopped at the winding start position. By performing these operations, the filamentous element 51 is wound crosswise around the inner tube 4. In the above-mentioned movement of the inner tube 4 in the second axial direction, the movement speed thereof is decreased gradually in the order of positions of the third region 223, the second region 222 and the first region 221.

Further, it is preferable that the absolute movement speed of the inner tube 4 over the respective regions 221, 222 and 223 is determined so as to be equal to each other in the two opposite (first and second) axial directions. By doing so, it is possible to obtain the same inclination angles $\theta 1$, $\theta 2$ and $\theta 3$ or the same lattice point intervals a1, a2 and a3 of the filamentous element 51 at the respective regions 221, 222 and 223, when the inner tube 4 is moved in both the axial directions.

Further, it is possible to determine the winding start position of the filamentous element 51 at the base end 21 of the catheter tube 2. Furthermore, in the above-mentioned example, although the rotative speed of the inner tube 4 is kept constant. However, even if the rotative speed of the inner tube 4 is changed in sequence at the first region 221, the second region 222 and the third region 223, respectively, while keeping the movement speed of the inner tube 4 at a constant value, the same inclination angles $\theta 1$, $\theta 2$ and $\theta 3$ or the same lattice point intervals a1, a2 and a3 of the filamentous element 51 can be obtained at the respective regions 221, 222 and 223.

Further, the same results can be obtained when the inner tube 4 is moved in both the axial directions two or more time, without being limited to only one reciprocal movement of the inner tube 4. Further, the number of filamentous elements 51 to be wound around the inner tube 4 is not limited to only one. It is also possible to wound a plurality of the filamentous elements 51 bundled together around the inner tube 4. Furthermore, it is also possible to wind around the inner tube 4 a plurality of filamentous elements 51 which are spaced away from each other at predetermined intervals in the axial direction of the catheter tube 2.

Further, the same results can be obtained by moving the inner tube 4 in only one direction (e.g., from the base end portion 21 to the tip portion 23) several times and by changing the rotational direction of the inner tube 4 such that the filamentous element 51 can be wound around the inner tube 4 in a intersectional manner.

Further, in the above-mentioned embodiment, the method in which the inner tube 4 is rotated and further moved in the axial direction thereof is adopted. Without being limited thereto, however, the same results can be obtained as far as the filamentous element supply device is rotated and further moved in the axial direction of the inner tube 4, relative to the inner tube 4. Therefore, the following modified combinations can be considered: (1) the inner tube 4 is rotated, and the filamentous element supply device is moved in the axial direction of the inner tube 4; (2) the inner tube 4 is moved in the axial direction thereof, and the filamentous element supply device is rotated around the outer circumferential surface of the inner tube 4; (3) the inner tube 4 is fixed, and the filamentous element supply device is rotated around the outer circumferential surface of the inner tube 4 and further moved in the axial direction of the inner tube 4; and (4) other appropriate combination of these method. Further, it is also possible to adopt the two different movement methods when any one of the inner tube and the filamentous element supply device is moved in both the first and second directions.

In accordance with the methods of forming the reinforcing material layer 5 as described above, it is possible to determine the lengths and the inclination angles $\theta 1$, $\theta 2$ and $\theta 3$ (i.e., the lattice point intervals a1, a2 and a3) of the filamentous element 51 to any desired values at the respective regions 221, 222 and 223, by appropriately adjusting only the relative movement speed and the relative rotational speed between the inner tube 4 and the filamentous element supply device. In other words, the rigidity of the catheter tube 2 can be adjustably determined to any desired value under well balanced conditions at the respective regions, so that it is possible to manufacture the various catheters which are suitable for various objects and various cases of diseases.

Further, since the inclination angles (i.e., lattice point intervals) of the filamentous element 51 can be changed continuously along the axial direction of the catheter tube 2 by only changing the relative movement speed and the relative rotational speed between the inner tube 4 and/or the filamentous element supply device continuously, it is possible to easily manufacture such a catheter tube in which the inclination angle of the filamentous element 51 can be changed continuously.

After the reinforcing material layer 5 is formed on the outer circumferential surface of the inner tube 4 as described above, the outer circumferential surface thereof is further covered by an outer tube 6. In this case, the outer tube 6 is joined with the inner tube 4 in such a way that the inner circumferential surface of the outer tube 6 is brought into tight contact with the outer circumferential surface of the inner tube 4 and the filamentous element 51. The joining methods of both elements are for instance as follows: the two tubes are bonded each other with the use of a bonding agent or a solvent; fused each other (e.g., thermal fusion, high-frequency fusion, etc.); connected each other by shrinkage after the inner tube 4 has been inserted into the heated or expanded (by solvent) outer tube 6; or alternatively the outer tube 6 is formed on the outer circumferential surface of the inner tube 4 by coating a melted or liquefied outer tube material and thereafter by solidifying the outer tube material through cooling or solvent removing treatment.

Thereafter, the outer surface of the outer tube 6 is covered with a hydrophilic high-molecular substance if necessary, and further the hub 7 is attached to the base end portion 21 of the catheter tube 2 according to the present invention to complete the catheter assembly 1.

EXAMPLE 1

A practical example of the catheter tube according to the present invention will be described hereinbelow.

The catheter tube for use of angiography as shown in FIGS. 1 to 4 was manufactured in accordance with the manufacturing method as already explained. The conditions at the respective portions are as follows: Further, the braider was used to form the reinforcing material layer.

Total length of catheter: 1000 mm

Length of first region 221: 125 mm

Length of second region 222: 125 mm

Length of third region 223: 650 mm

Length of tip portion 23: 100 mm

Outer diameter of outer tube 6: 1.7 mm

Outer diameter of inner tube 4: 1.5 mm

Inner diameter of inner tube 4: 1.1 mm

Material of outer tube 6: Polyurethane mixed with contrast medium (Shore D hardness=65)

Material of inner tube 4: The same as outer tube 6

Outer surface of outer tube 6: Coated with anhydrous maleic acid copolymer

Material of filamentous element 51: Stainless steel

Diameter of filamentous element 51: 50 μm

Inclination angles θ1, θ2 and θ3: Listed in Table 1

Lattice point intervals a1, a2 and a3: Listed in Table 1

Figure 6:
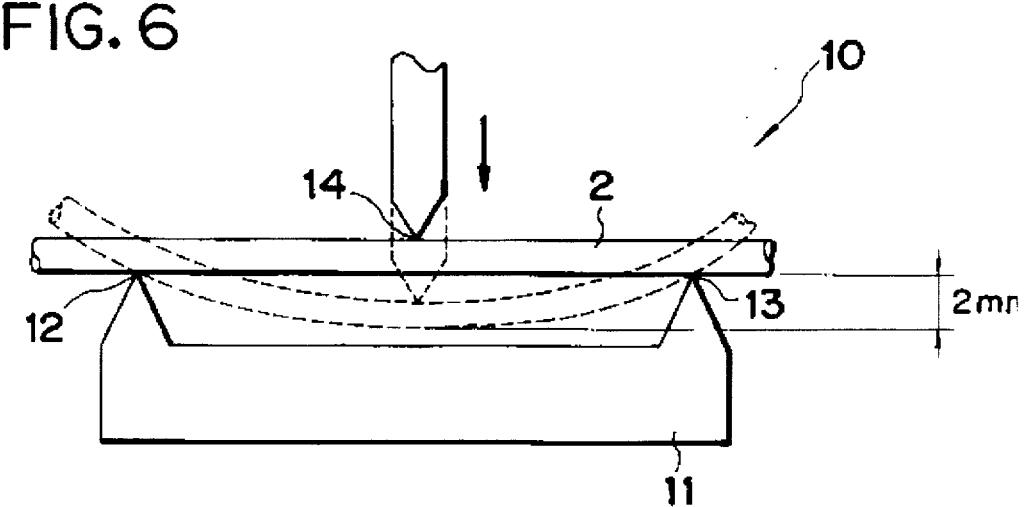
FIG. 6 is a front view showing a condition in which a test is conducted on the embodiment of the catheter tube of the present invention by using a jig.

In order to test the rigidity of this catheter tube at the respective positions, a jig 10 as shown in FIG. 6 was used. In test, the first region 221 (extended into a straight line) of the catheter 2 was mounted between two edges 12 and 13 (the interval between the edges=1 inch) of a base 11 of the jig 10. Under the condition, the middle portion of the first region 221 is pushed downwardly by 2 mm with another edge 14, and a load required to push the middle portion was measured. The same measuring was conducted to the tip portion 23, the second and third regions 222 and 223, respectively. These test results are listed in Table 1. Further, the test was made at room temperature (about 20° C.) and under a fixed temperature (37° C. roughly near the body temp.)

TABLE 1

|  | Tip portion 23 | First region 221 | Second region 222 | Third region 223 |
| --- | --- | --- | --- | --- |
| Inclination angles | — | θ1 = 50° | θ2 = 44° | θ3 = 37° |
| Lattice point intervals | — | a1 = 0.4 mm | a2 = 0.6 mm | a3 = 0.8 mm |
| At room temp (20° C.) | 28.5 g | 33.3 g | 40.5 g | 77.0 g |
| Under a fixed (37° C.) | 16.0 g | 17.8 g | 23.5 g | 51.4 g |

As listed in Table 1, it has been confirmed that the bending elastic modulus of the catheter tube decreases in accordance with increase of the inclination angle or decrease of the lattice point interval of the filamentous element 51 toward the tip of the catheter tube 1.

EXAMPLE 2

A catheter tube which is the same as that of Example 1 excepting that the filamentous element 51 was formed by a tungsten wire with a diameter of 50 μm was manufactured and measurement was made in the same way. The obtained test results are the same as in Table 1, and it has been confirmed that the bending elastic modulus of the catheter tube decreases in accordance with increase of the inclination angle or decrease of the lattice point interval of the filamentous element 51 toward the tip of the catheter tube.

EXAMPLE 3

Catheter tubes which are the same as those of Examples 1 and 2, excepting that the outer diameter of the outer tube 6 was decreased gradually from the second region 222 to the tip of the catheter tube 2 (the outer diameter of the catheter tip: 1.6 mm), were manufactured and measurement was made in the same way. The obtained test results are the same as in Table 1, and it has been confirmed that the bending elastic modulus of the catheter tube decreases in accordance with increase of the inclination angle or decrease of the lattice point interval of the filamentous element 51 toward the tip of the catheter tube.

EXAMPLE 4

Catheter tubes which are the same as those of Examples 1 to 3, excepting that the material of the inner tube 4 was polyamide elastomer (Shore D hardness=55) and the material of the outer tube 6 was polyamide elastomer (Shore D hardness=40), were manufactured and measurement was made in the same way. The obtained test results are the same as in Table 1, and it has been confirmed that the bending elastic modulus of the catheter tube decreases in accordance with increase of the inclination angle or decrease of the lattice point interval of the filamentous element 51 toward the tip of the catheter tube.

Finally, it should be noted that this invention is no limited to the above-described embodiment of the present invention, and many modifications and variations can be made within the teaching of the present invention. Accordingly, the scope of the present invention will be determined only by the appended claims.

What is claimed is:

1. A catheter tube having a longitudinal axis, a first end for attachment to a hub and a tip portion at an opposite end thereof, comprising:

a flexible inner tube;

a flexible outer tube provided around said inner tube; and a reinforcing material layer disposed between said inner and outer tubes along substantially the entire length of said tubes excepting said tip portion for imparting appropriate rigidity to the catheter tube, said reinforcing material layer having a front side thereof adjacent to the tip portion of the catheter tube, wherein said reinforcing material layer is formed by arranging at least one filamentous element in a lattice manner in such a way that the inclination angles of the filamentous element with respect to the axis of the catheter tube change continuously or in a stepwise manner along the axial direction so as to form one section thereof in which the inclination angle is relatively large and another section thereof in which the inclination angle is relatively small, wherein said filamentous element is formed of a single wire or by bundling a plurality of wires, whereby the bending rigidity of the catheter tube at which said one section of said reinforcing material layer is located becomes smaller in comparison with that of the catheter tube at which said another section of said reinforcing material layer is located, and wherein said one section of said reinforcing material layer is located at least at the front side of said reinforcing material layer in such a manner that the bending rigidity of the catheter tube is continuously reduced toward said tip portion; and wherein said reinforcing material layer has a tip portion, and a thickness of said outer tube or said inner tube decreases near the tip portion of said reinforcing material layer.

2. The catheter tube as claimed in claim 1, wherein said inner and outer tubes are formed of the same material.

3. The catheter tube as claimed in claim 1, wherein at least said outer tube is formed of a soft material.

4. A catheter tube having a longitudinal axis, a first end for attachment to a hub and a tip portion at an opposite end thereof, comprising:

a flexible inner tube;

a flexible outer tube provided around said inner tube; and a reinforcing material layer disposed between said inner and outer tubes along substantially the entire length of said tubes excepting said tip portion for imparting appropriate rigidity to the catheter tube, said reinforcing material layer having a front side thereof adjacent to the tip portion of the catheter tube, wherein said reinforcing material layer is formed by arranging at least one filamentous element in a lattice manner in such a way that the intervals of the lattice points of said filamentous element along the axial direction of the catheter tube change continuously or in a stepwise manner along the axial direction of the catheter tube so as to form one section thereof in which the respective interval between the lattice points of the filamentous element is relatively small and another section thereof in which the respective interval between the lattice points of the filamentous element is relatively large, and wherein said reinforcing material layer has a tip portion, and a thickness of said outer tube or said inner tube decreases near the tip portion of said reinforcing material layer, wherein said filamentous element is formed of a single wire or by bundling a plurality of wires, whereby the bending rigidity of the catheter tube at which said one section of said reinforcing material layer is located becomes smaller in comparison with that of the catheter tube at which said another section of said reinforcing material layer is located, and wherein said one section of said reinforcing material layer is located at least at the front side of said reinforcing material layer in such a manner that the bending rigidity of the catheter tube is continuously reduced toward said tip portion.

5. The catheter tube as claimed in claim 4, wherein said inner and outer tubes are formed of the same material.

6. The catheter tube as claimed in claim 5, wherein said catheter tube has an outer surface thereof, and the outer surface of said catheter tube is covered with a hydrophilic high-molecular substance.

7. The catheter tube as claimed in claim 4, wherein at least said outer tube is formed of a soft material.

8. The catheter tube as claimed in claim 7, wherein said catheter tube has an outer surface thereof, and the outer surface of said catheter tube is covered with a hydrophilic high-molecular substance.

9. A catheter tube having a longitudinal axis, a first end for attachment to a hub and a tip portion at an opposite end thereof, comprising:

a flexible inner tube;

a flexible outer tube provided around said inner tube; and a reinforcing material layer disposed between said inner and outer tubes along substantially the entire length of said tubes excepting said tip portion for imparting appropriate rigidity to the catheter tube, said reinforcing material layer having a front side thereof adjacent to the tip portion of the catheter tube, wherein said reinforcing material layer is formed by arranging at least one filamentous element in a lattice manner in such a way that the inclination angles of the filamentous element with respect to the axis of the catheter tube change continuously or in a stepwise manner along the axial direction so as to form one section thereof in which the inclination angle is relatively large and another section thereof in which the inclination angle is relatively small, and wherein said reinforcing material layer has a tip portion and a thickness of said outer tube or said inner tube decreases near the tip portion of said reinforcing material layer, wherein said filamentous element is formed of a single wire or by bundling a plurality of wires, wherein sections of the catheter tube containing the filamentous element having relatively larger inclination angles are more flexible in comparison with sections thereof containing the filamentous element having the relatively small inclination angles, and wherein said one section of said reinforcing material layer is located at least at the front side of said reinforcing material layer in such a manner that the bending rigidity of the catheter tube is continuously reduced toward said tip portion.

10. The catheter tube as claimed in one of claims 2, 3 or 9 wherein said catheter tube has an outer surface thereof, and the outer surface of said catheter tube is covered with a hydrophilic high-molecular substance.

* * * * *

UNITED STATES PATENT AND TRADEMARK OFFICE
CERTIFICATE OF CORRECTION

PATENT NO. : 5,538,513
DATED : July 23, 1996
INVENTOR(S) : Naofumi OKAJIMA

It is certified that error appears in the above-indentified patent and that said Letters Patent is hereby corrected as shown below:

In Section [57], kindly delete "$\theta1 < \theta2 < \theta3$" and insert -- $\theta1 > \theta2 > \theta3$ --.

In Column 7, line 64, delete "polymide" and insert -- polyimide --.

In Column 8, line 65, delete "hydroxyproyl" and insert -- hydroxypropyl --.

In Column 12, line 6, after "stainless steel" insert -- (SUS 316) --.

In Column 16, line 6, delete "2, 3" and insert -- 1, 4 --.

Signed and Sealed this

Twenty-fifth Day of March, 19

Attest:

BRUCE LEHMAN

Attesting Officer     Commissioner of Patents and Trademarks